United States Patent
Bonner et al.

(10) Patent No.: US 9,097,724 B2
(45) Date of Patent: Aug. 4, 2015

(54) SYSTEMS AND METHODS FOR SEQUENCING PEPTIDES BY MASS SPECTROMETRY

(71) Applicant: DH TECHNOLOGIES DEVELOPMENT PTE. LTD., Singapore (SG)

(72) Inventors: Ronald F. Bonner, Newmarket (CA); Stephen A. Tate, Barrie (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 14/368,872

(22) PCT Filed: Dec. 4, 2012

(86) PCT No.: PCT/IB2012/002584
§ 371 (c)(1),
(2) Date: Jun. 26, 2014

(87) PCT Pub. No.: WO2013/098609
PCT Pub. Date: Jul. 4, 2013

(65) Prior Publication Data
US 2015/0129758 A1    May 14, 2015

Related U.S. Application Data

(60) Provisional application No. 61/582,041, filed on Dec. 30, 2011.

(51) Int. Cl.
*H01J 49/26*    (2006.01)
*G01N 33/68*    (2006.01)
*H01J 49/00*    (2006.01)

(52) U.S. Cl.
CPC .......... *G01N 33/6848* (2013.01); *H01J 49/004* (2013.01); *H01J 49/0036* (2013.01)

(58) Field of Classification Search
USPC .................................................. 250/281, 282
See application file for complete search history.

(56) References Cited

U.S. PATENT DOCUMENTS 5,686,726 A    11/1997    Fenn et al.
6,734,294 B2 *    5/2004    Nelson et al. ................ 536/22.1
(Continued)

FOREIGN PATENT DOCUMENTS

EP    1047108 B1    3/2006

OTHER PUBLICATIONS

International Search Report for PCT/IB2012/002584, mailed May 16, 2013.

*Primary Examiner* — Kiet T Nguyen
(74) *Attorney, Agent, or Firm* — John R. Kasha; Kelly L. Kasha; Kasha Law LLC

(57) ABSTRACT

The number of atoms present in an ion of a molecule is identified using a mixture of different forms of the molecule. A mass spectrometer analyzes a mixture of at least two forms of the molecule using one or more ion scans producing a mass spectrum. The first form of the molecule includes a first combination of isotopes of one or more elements. The second form of the molecule includes a second combination of isotopes of the one or more elements. A first peak and a second peak that differ in mass by a multiple of a mass difference between the first combination of isotopes and the second combination of isotopes are located in the mass spectrum. The number of atoms of the one or more elements present in an ion of the molecule is identified from a mass difference between the first peak and the second peak.

18 Claims, 14 Drawing Sheets

(56) References Cited

U.S. PATENT DOCUMENTS

| | | |
|---|---|---|
| 2004/0096982 A1 | 5/2004 | Barnea et al. |
| 2007/0154900 A1 | 7/2007 | Schneider et al. |
| 2010/0096545 A1 | 4/2010 | Malek et al. |
| 2011/0084204 A1* | 4/2011 | Beecher ................. 250/282 |

* cited by examiner

| | |
|---|---|
| 159.09211 | C10H11N2, C7H15N2S |
| 185.16669 | C10H21N2O |
| 213.16158 | C11H21N2O2 |
| 246.12673 | C10H20N3O2S, C13H16N3O2 |
| 274.12058 | C11H20N3O3S, C14H16N3O3, C7H20N3O8 |
| 300.19482 | C14H26N3O4 |

600

| N | m/z | 16 421.23 | 16 523.226 | 16 727.311 | 16 1453.61 |
|---|---|---|---|---|---|
| 14 | 634.2725 | | | 93.0382 | |
| 14 | 857.3854 | | | | |
| 14 | 895.4335 | | | | |
| 14 | 1,185.62 | | | | |
| 14 | 1,249.53 | | | | |
| 14 | 1,267.54 | | | | 186.0742 |
| 14 | 1,477.63 | | | | |
| | | | W | 186.079 | |

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial sequence
<220> FEATURE:
<223> OTHER INFORMATION: Yeast

<400> SEQUENCE: 1

Leu Val Ser Trp Tyr Asp Asn Glu Tyr Gly Tyr Ser Thr Arg
1               5                   10
```

SYSTEMS AND METHODS FOR SEQUENCING PEPTIDES BY MASS SPECTROMETRY

RELATED APPLICATION

This application claims priority to U.S. provisional application No. 61/582,041, filed Dec. 30, 2011, which is incorporated herein by reference in its entirety.

INTRODUCTION

Determining the sequence of a peptide based solely on the masses of fragments obtained by tandem mass spectrometry, or mass spectrometry/mass spectrometry (MS/MS), is known as "de novo sequencing." De novo sequencing is important when conventional data base searching approaches fail. Conventional data base searching approaches fail, for example, because the protein is unknown, modified, mutated, or comes from an unknown genome.

De novo sequencing involves obtaining accurate masses for fragments and looking for fragment ions that differ by the masses of amino acids so that a "sequence" tag is determined. If the tag is traced to the N- or C-terminus then an appropriate terminal sequence is defined. In practice this is difficult for a number of reasons. These reasons include insufficient mass accuracy, isobaric sequences (e.g. GT has the same composition as AS), inability to distinguish the sequence direction (b vs. y), and difficulty in distinguishing sequence ions from secondary fragments (such as loss of water from a side chain). These reasons also include unexpected fragmentation, gaps in the ladder, and unexpected/unknown modifications.

The direction or orientation of a sequence can be determined if the sequence ions can be assigned to the b or y series. B ions contain the original N-terminus of the peptide and y ions contain the C terminus. Peptides are typically produced by digesting a protein with trypsin which cleaves at lysine (Lys, K) or arginine (Arg, R) so that the first y ion (y1) must be either of these residues. Thus if sequence ions can be traced to the y1 ion they are members of the y-ion series. The N-terminus can be any residue except K or R, so the b1 ion does not have a definite identity. B ions, however, commonly undergo additional fragmentation and lose CO producing a corresponding a ion so the presence of peaks separated by the mass of CO (27.99419) identifies the higher mass ion as a b ion.

It has been proposed that the amino acid composition be determined in order to avoid some of the problems associated with de novo sequencing. Such an approach, however, still requires very high mass accuracy data.

SUMMARY

According to various embodiments of the applicant's teachings, a system for identifying the number of atoms present in an ion of a molecule using a mixture of different forms of the molecule, comprising a mass spectrometer that analyzes a mixture of at least two forms of a molecule using one or more ion scans across a mass range and produces a mass spectrum from the one or more ion scans for the mass range, wherein a first form of the molecule includes a first combination of isotopes of one or more elements, and, wherein a second form of the molecule includes a second combination of isotopes of the one or more elements; and a processor in communication with the mass spectrometer that locates a first peak and a second peak in the mass spectrum that differ in mass by a multiple of a mass difference between the first combination of isotopes and the second combination of isotopes, and identifies a number of atoms of the one or more elements present in an ion of the molecule from a mass difference between the first peak and the second peak.

According to various embodiments of the applicant's teachings, the processor further locates a first peak and a second peak in the mass spectrum that differ in mass by a multiple of a mass difference between the first isotope and the second isotope and that have an intensity ratio substantially equal to the ratio of the amounts of the first form of the molecule and the second form of the molecule in the mixture.

According to various aspects of the applicant's teachings, said one or more elements comprises an element, said first combination of isotopes comprises a first isotope of the element, said second combination of isotopes comprises a second isotope of the element, and the processor locates a first peak and a second peak in the mass spectrum that differ in mass by a multiple of a mass difference between the first isotope and the second isotope and identifies a number of atoms of the element from the multiple.

According to various aspects of the applicant's teachings, the one or more elements are selected from the group consisting of nitrogen (N), carbon (C), hydrogen (H), oxygen (O), and sulfur (S).

According to various embodiments of the applicant's teachings, when one or more elements comprise nitrogen (N), the first combination of isotopes comprises 14N and the second combination of isotopes comprises 15N; wherein when one or more elements comprise carbon (C), the first combination of isotopes comprises 12C and the second combination of isotopes comprises 13C; wherein when one or more elements comprise hydrogen (H), the first combination of isotopes comprises 1H and the second combination of isotopes comprises 2H; wherein when one or more elements comprise oxygen (O), the first combination of isotopes comprises 16O and the second combination of isotopes comprises 18O; and wherein when one or more elements comprise sulfur (S), the first combination of isotopes comprises 32S and the second combination of isotopes comprises 34S.

According to various aspects of the applicant's teachings, isotope labeling can be used to create the first form of the molecule and the second form of the molecule in the mixture.

According to various embodiments of the applicant's teachings, the mass spectrometer comprises a tandem mass spectrometer and the ion of the molecule comprises a product ion of a precursor ion obtained by tandem mass spectrometry/mass spectrometry (MS/MS).

According to various aspects of the applicant's teachings, the precursor ion comprises a peptide and the product ion comprises a peptide sequence ion.

According to various embodiments of the applicant's teachings, the processor uses the peptide sequence ion to determine a sequence of the peptide.

According to various aspects of the applicant's teachings, the first peak and the second peak comprise a first peak pair and the processor determines a sequence of the peptide by locating a second peak pair that differ in mass by a multiple of a mass difference between the first combination of isotopes and the second combination of isotopes, identifying a second number of atoms of the one or more elements present in a second ion of the molecule from, a mass difference between peaks of the second peak pair, and determining an amino acid residue of the sequence if a mass difference between a first mass of the first peak pair and a second mass of the second peak pair is substantially equal to a mass of the amino acid and if a difference between the number of atoms of the one or more elements and the second number of atoms of the one or more elements is equal to a number of atoms of the one or more elements in the amino acid residue.

According to various aspects of the applicant's teachings, the first mass of the first peak pair is a low mass of the first peak pair and the second mass of the second peak pair is a low mass of the second peak pair, or wherein the first mass of the first peak pair is a high mass of the first peak pair and the second mass of the second peak pair is a high mass of the second peak pair.

According to various embodiments of the applicant's teachings, the processor further locates a terminus of the sequence.

According to various aspects of the applicant's teachings, the processor locates a terminus of the sequence by locating a peak pair of the sequence that includes a mass that is substantially equal to one amino acid residue or that includes a mass that is substantially equal to a mass of the peptide.

According to various aspects of the applicant's teachings, the processor further determines an orientation of the sequence from the terminus.

According to various aspects of the applicant's teachings, the processor determines an orientation of the sequence from the terminus by calculating a terminus mass of the terminus amino acid residue and a terminus number of atoms of the one or more elements present in the terminus amino acid residue and determining that the orientation is C-terminal if the peptide is from a tryptic digestion and the terminus mass and the terminus number of atoms correspond to Arg or Lys.

According to various aspects of the applicant's teachings, the processor determines an orientation of the sequence from the terminus by calculating a terminus mass of the terminus amino acid residue and determining that the orientation is N-terminal if another peak is found at another mass that is substantially equal the terminus mass minus a mass of CO (27.99419 amu).

According to various aspects of the applicant's teachings, a method for identifying the number of atoms present in an ion of a molecule using a mixture of different forms of the molecule, comprising obtaining a mass spectrum produced by a mass spectrometer that analyzes a mixture of at least two forms of a molecule using one or more ion scans across a mass range, wherein a first form of the molecule includes a first combination of isotopes of one or more elements, and wherein a second form of the molecule includes a second combination of isotopes of the one or more elements; locating a first peak and a second peak in the mass spectrum that differ in mass by a multiple of a mass difference between the first combination of isotopes and the second combination of isotopes; and identifying a number of atoms of the one or more elements present in an ion of the molecule from a mass difference between the first peak and the second peak.

According to various aspects of the applicant's teachings, a computer program product, comprising a non-transitory and tangible computer-readable storage medium whose contents include a program with instructions being executed on a processor so as to perform a method for identifying the number of atoms present in an ion of a molecule using a mixture of different forms of the molecule, the method comprising providing a system, wherein the system comprises one or more distinct software modules, and wherein the distinct software modules comprise a measurement module and an identification module; obtaining a mass spectrum produced by a mass spectrometer that analyzes a mixture of at least two forms of a molecule using one or more ion scans across a mass range using the measurement module, wherein a first form of the molecule includes a first combination of isotopes of one or more elements, and wherein a second form of the molecule includes a second combination of isotopes of the one or more elements; locating a first peak and a second peak in the mass spectrum that differ in mass by a multiple of a mass difference between the first combination of isotopes and the second combination of isotopes using the identification module; and identifying a number of atoms of the one or more elements present in an ion of the molecule from a mass difference between the first peak and the second peak using the identification module.

BRIEF DESCRIPTION OF THE DRAWINGS

The skilled artisan will understand that the drawings, described below, are for illustration purposes only. The drawings are not intended to limit the scope of the present teachings in any way.

Figure 1:
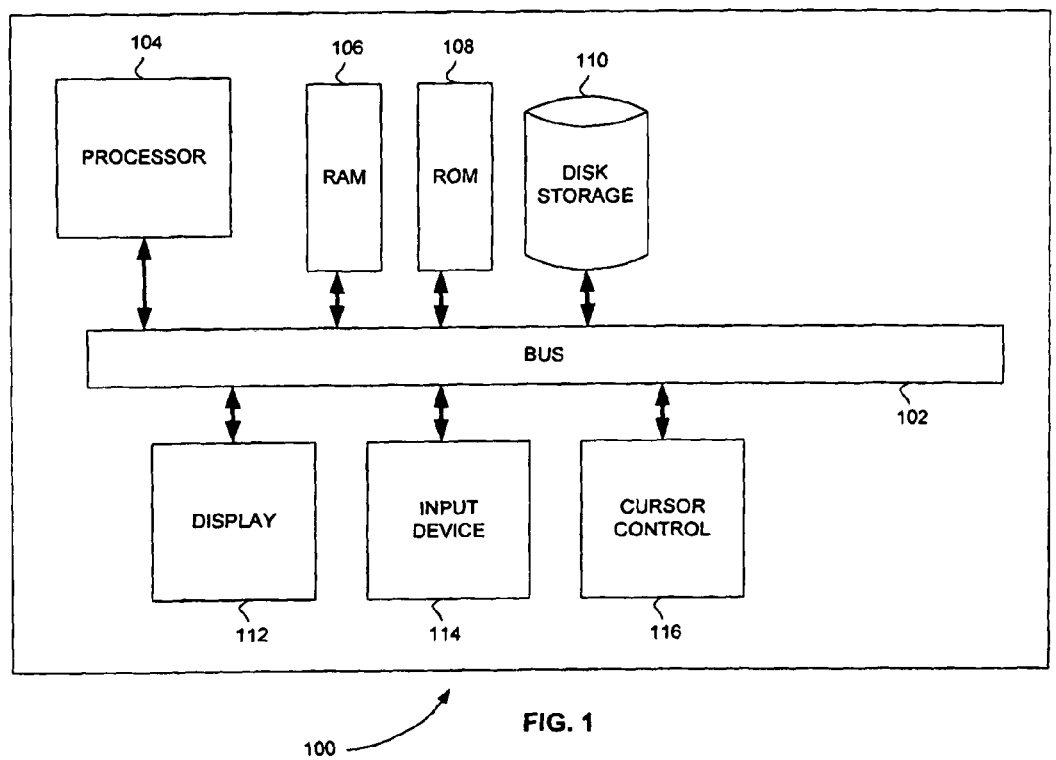
FIG. 1 is a block diagram that illustrates a computer system, in accordance with various embodiments.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a network. The remote computer can receive data over the network and place the data on bus 102. Bug 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

De Novo Sequencing

As described above, de novo sequencing, or determining the sequence of a peptide based solely on the masses of fragments obtained by tandem mass spectrometry, or mass spectrometry/mass spectrometry (MS/MS), is difficult for a number of reasons. However, if information about the amino acid composition can be determined, many of the difficulties of de novo sequencing can be overcome.

Although the various embodiments described below relate preferably to identification of peptides or proteins, they also apply to other kinds of molecules. In other words, other kinds of molecules can be identified from their fragments using the various embodiments described below.

In various embodiments, knowledge of how many atoms of a particular element are present in a peptide fragment dramatically limits the number of possible amino acid combinations that need to be considered. For example, all amino acid residues are known to have one nitrogen atom. Some residues, however, have two, three, or four nitrogen atoms. Therefore, determining the number of nitrogen atoms in a peptide fragment can reduce the number of possible amino acid sequence combinations that need to be analyzed.

In various embodiments, determination of how many atoms of a particular element are present in a peptide fragment is accomplished by analyzing an MS/MS spectrum for two or more peaks from different forms of the peptide fragment that include different isotopes of a particular element. A pair of peaks from two different forms of the peptide fragment can be called a doublet. A doublet is located, for example, by analyzing the spacing between two peaks. When the spacing between two peaks is a multiple of a mass difference between two isotopes of the element, a doublet is found. The multiple of the mass difference for the doublet found is then the number of atoms of the particular element in the peptide fragment.

Doublet peaks occur, for example, when an analyzed sample includes a mixture of two forms of the same peptide or protein that contain two different isotopes of the same element. The relative intensities of the doublet peaks reflect the relative concentrations of the two different forms of the peptide fragments in the mixture.

In order to identify doublet peaks a combined spectrum containing fragments for the labeled and unlabeled forms of the same peptide must be obtained and analyzed or plotted together. The combined spectrum can be obtained by adding together MS/MS spectra obtained for the two forms separately using precursor mass selection widths of ca. 1 amu or by using a wide selection window that contains both precursor ions. The wide window can be 25 amu for example. The wide window width can be fixed or variable. Performing two or more adjacent MS scans across a mass range is called sequential windowed acquisition (SWATH) mass spectrometry (MS) analysis, for example.

Data Examples

In one exemplary embodiment, knowledge of the number of nitrogen atoms contained in a fragment ion is used to dramatically limit the number of possible fragment amino acid combinations. This additional information is obtained from a SWATH MS analysis of a mixture of 14N and 15N labeled peptides, for example.

Typical isotope labeling methods, such as stable isotope labeling with amino acids in cell culture (SILAC), add a tag with a fixed mass to a specific amino acid so that the precursor ion and all fragments containing the tag are shifted by the same amount. In contrast, when yeast is grown on 15N labeled NH4SO4, every nitrogen atom causes a mass shift and so the mass observed depends on the number of nitrogen atoms in the ion. If the 15N and 14N labeled forms are analyzed together, pairs of peaks with different spacing are readily observed.

Figure 2:
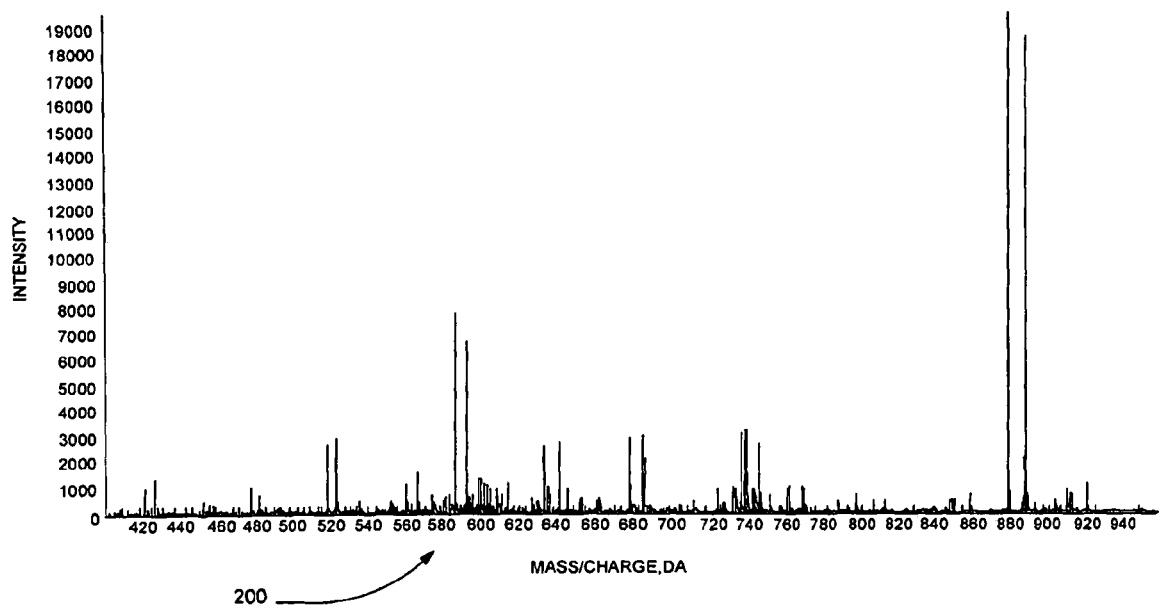
FIG. 2 is an exemplary plot of a mass spectrometry (MS) spectrum from the tryptic digest of an approximately equal mixture of 15N and 14N labeled proteins, in accordance with various embodiments.

FIG. 2 is an exemplary plot 200 of an MS spectrum from the tryptic digest of an approximately equal mixture of 15N and 14N labeled proteins, in accordance with various embodiments. Plot 200 shows a single MS spectrum obtained from the analysis of such a sample mixture where the presence of many doublet peaks (876.9/886.4, 736.3/744.3, 676.8/684.3, etc.) is apparent. It is also apparent that as the mass of doublet peaks increases, the spacing between peaks also increases, since there are more nitrogen atoms in the ions.

Figure 3:
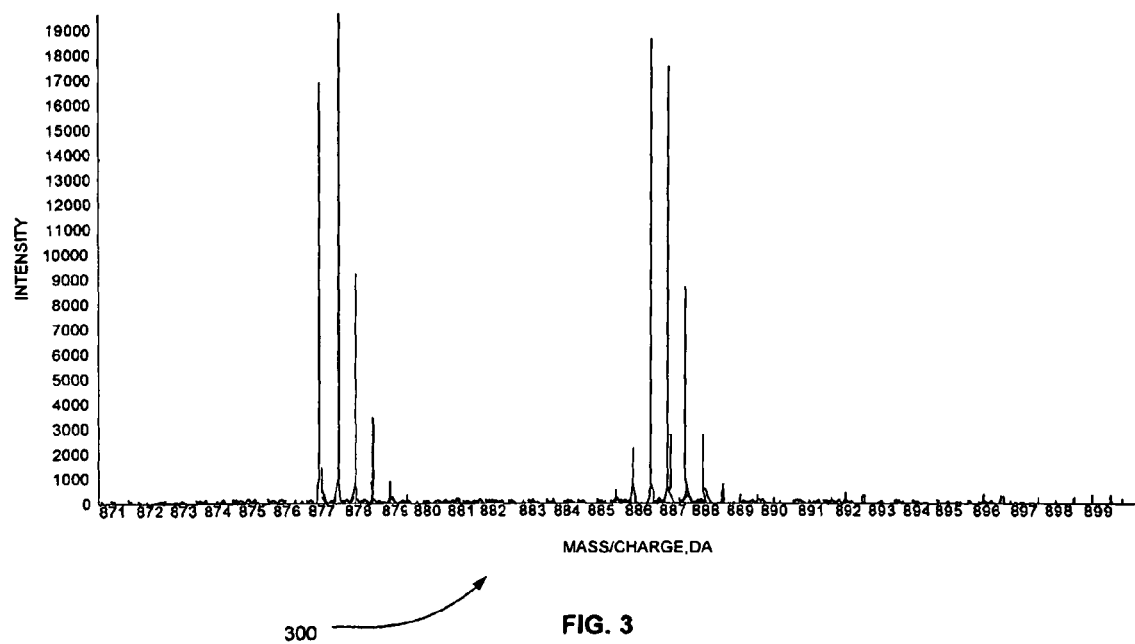
FIG. 3 is an exemplary plot of an expanded region of the MS spectrum of FIG. 2, in accordance with various embodiments.

FIG. 3 is an exemplary plot 300 of an expanded region of the MS spectrum of FIG. 2, in accordance with various embodiments. Plot 300 shows a doublet that includes masses 876.9002 and 886.3723. An arrow is placed on the peak at 876.9002 to generate relative labeling. The doublet appears with a difference or delta of 9.4721, which corresponds to 18.9442, since these are doubly charged ions. The mass of 15N is 15.0001 and that of 14N is 14.00307, giving an expected difference of 0.99704 per nitrogen atom, so a difference of 18.9442 corresponds to 19.00044 N atoms.

Using a doubly charged mass of 876.9002 and allowing for an error of 5 part per million (ppm) and a maximum composition C100.H500.O30.N30.S10, generates 778 possible elemental compositions. 10 ppm produces more than 10,000 compositions. If, however, the nitrogen content is set to 19 there are only 26 possible compositions at 5 ppm and 49 at 10 ppm.

The fact that the 15N-14N mass difference is slightly less than one is helpful in ensuring that real members of a pair are identified. For the 2 forms above, the mass deficiencies are 0.7844 (14N) and 0.7290 (15N) with a delta of 56 mmu, which can be separated at this mass with a resolution of approximately 30,000, suggesting that 15N and 14N peptides at the same mass are likely to be resolved.

In addition, there is a small peak in front of the main peak of the 15N form (885.8718 in this case. This peak is due to the fact that the 15N ammonium sulphate contains a small amount of 14N.

Thus there are several ways to correctly identify the 15N-14N pairs in this exemplary embodiment. First of all, the mass delta must correspond to an integral multiple of 0.99704, the difference between the masses of 15N and 14N. Secondly, there is likely to be a small satellite peak at the low mass end of the 15N peak cluster. So, if the purity of the 15N is known, the intensity of this peak can be predicted. Finally, the intensity of the monoisotopic peaks should reflect the relative amounts of their proteins in the mixture. In this example, the relative amounts of the different forms of proteins were mixed with a 1:1 ratio.

The behavior of monoisotopic peaks extends to fragments also. Fragment ions occur in pairs, and the mass difference directly indicates the number of nitrogen atoms in the ions. However, in order to observe these ion pairs, both the 15N and 14N precursors must be fragmented. Since the spacing is not known in advance, a data independent method of acquisition is used. SWATH MS analysis is performed where 25 amu mass window widths of the mass range are fragmented together and any 15N/14N pairs in this window generate fragments. Since the ions most frequently observed from tryptic digests are doubly charged, mass differences up to 50 (50 nitrogen atoms) can be seen. In the analysis of a real sample by LCMS, however, there are inevitably cases where the two forms of a peptide are observed in separate mass windows, but this can be accommodated by combining the spectra from different mass window widths.

Figure 4:
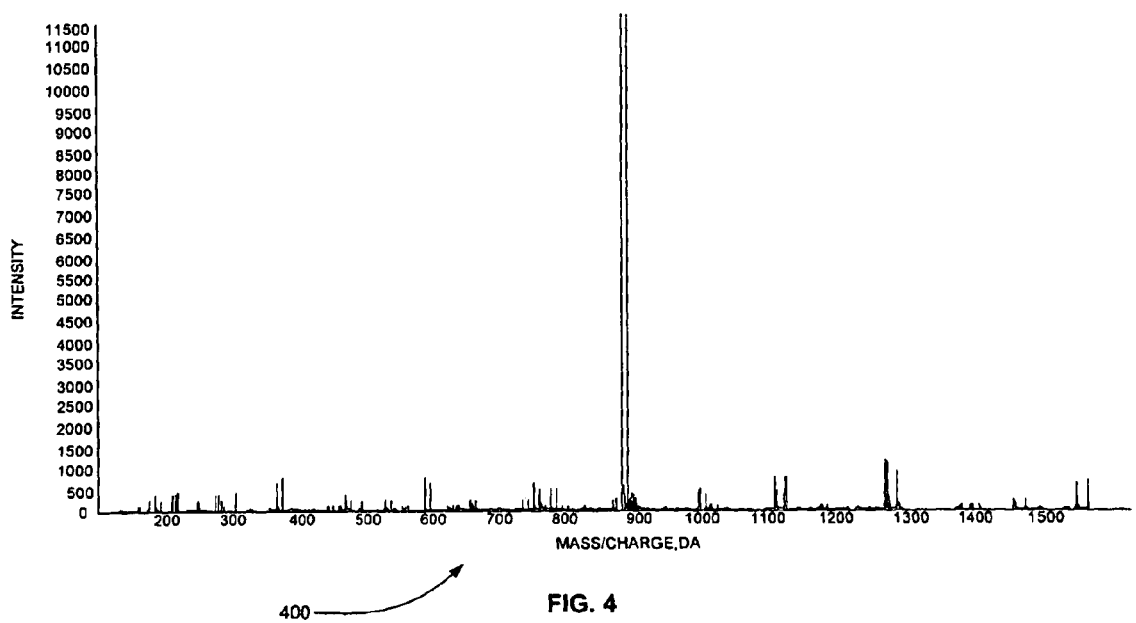
FIG. 4 is an exemplary plot of a mass spectrometry/mass spectrometry (MS/MS) spectrum obtained by fragmenting a mass window that includes the doublet shown in FIG. 3, in accordance with various embodiments.

FIG. 4 is an exemplary plot 400 of an MS/MS spectrum obtained by fragmenting a mass window that includes the doublet shown in FIG. 3, in accordance with various embodiments. Doublet peaks are again readily apparent in plot 400. Also apparent in plot 400, is the fact that the spacing between doublet peaks increases with mass and the number of nitrogen atoms.

Figure 5:
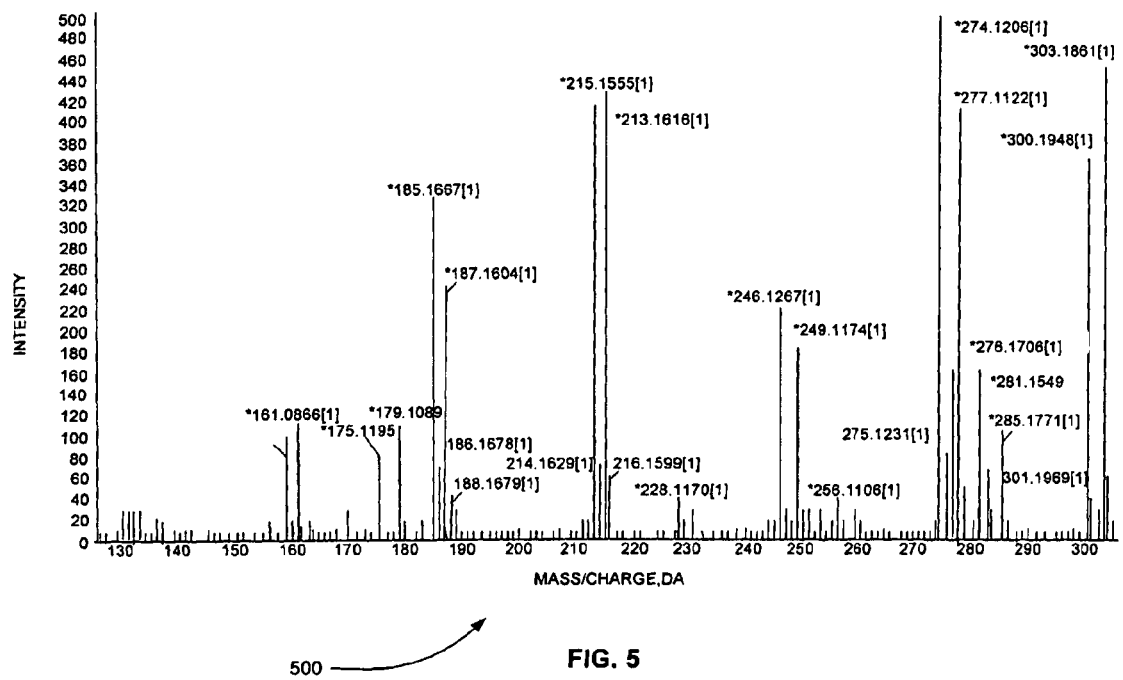
FIG. 5 is an exemplary plot of a low mass region of the MS/MS spectrum shown in FIG. 4, in accordance with various embodiments.

FIG. 5 is an exemplary plot 500 of a low mass region of the MS/MS spectrum shown in FIG. 4, in accordance with various embodiments. In plot 500, most of the doublet peaks are separated by 2 (159/161, 185/187, 213/215) or 3 (246/249, 274/277, 300/303) nitrogen atoms. A notable exception is the pair 175.1195/179.1089 with a gap of 4 corresponding to four nitrogen atoms. The mass of 175.1195 generates only one composition with 4 nitrogen atoms even at 100 ppm accuracy, compared to 20 when this is not specified. The elemental composition is $C_6H_{15}N_4O_2$, corresponding to the y1 ion of Arg. Further, the ion pair at 276.1706/281.1549 contains 5 nitrogen atoms, so the difference between the 175.1195 and 276.1706 peaks could correspond to the next ion formed by the addition of an amino acid residue with a mass of 101.0511 and one nitrogen atom, i.e. threonine, $C_4H_7NO_2$, with a mass of 101.048.

Figure 6:
FIG. 6 is an exemplary table showing other elemental compositions obtained for ions in the region shown in FIG. 5 using a match tolerance of 20 ppm, in accordance with various embodiments.

FIG. 6 is an exemplary table 600 showing other elemental compositions obtained for ions in the region shown in FIG. 5 using 20 ppm, in accordance with various embodiments. The nitrogen atom count is apparent for each elemental composition. Table 600 shows that none of these elemental compositions can be y ions, since none of them have at least the N4 of the ion at 175. Also, the a/b relationships (a difference of 27.9947 corresponding to CO) are clear for 185/213 and 246/274 (although the difference between these "b" ions does not correspond to an amino acid. This may be due to scrambling or internal fragments, for example. Since the elemental compositions of adjacent sequence ions must differ by at least one nitrogen atom, we can examine the compositions containing 2 and 3 N atoms to find any that correspond to amino acids. In this case the compositions for mass 213.16158 and 300.19482 differ by the composition C3H5NO2 which corresponds to the amino acid serine (S, 87.032). Hence these ions identify part of the b ion sequence and the difference is due to the addition of a serine residue.

Figure 7:
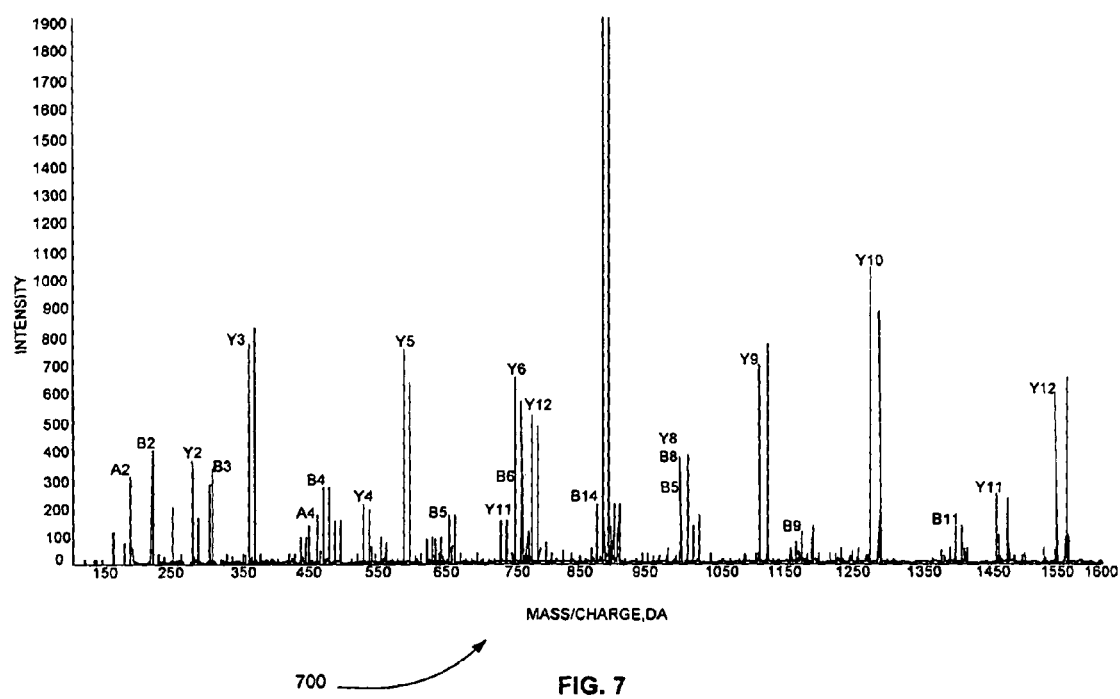
FIG. 7 is an exemplary plot of the spectrum of the 15N/14N pairs that identify the sequence ions of peptide LVSWYD-NEYGYSTR, in accordance with various embodiments.

FIG. 7 is an exemplary plot 700 of the spectrum of the 15N/14N pairs that identify the sequence ions of peptide LVSWYDNEYGYSTR, in accordance with various embodiments. Plot 700 also includes ion pairs that are not labeled, even though they are peptide related. These ion pairs arise from unexpected fragments, internal fragments, b ion scrambling, or from another peptide fragmenting in the same mass window width. An elemental composition that is available provides an opportunity to identify these ions.

In various embodiments, knowledge of the N atom count for each ion pair introduces new ways of visualizing and interpreting peptide MSMS spectra.

Figure 8:
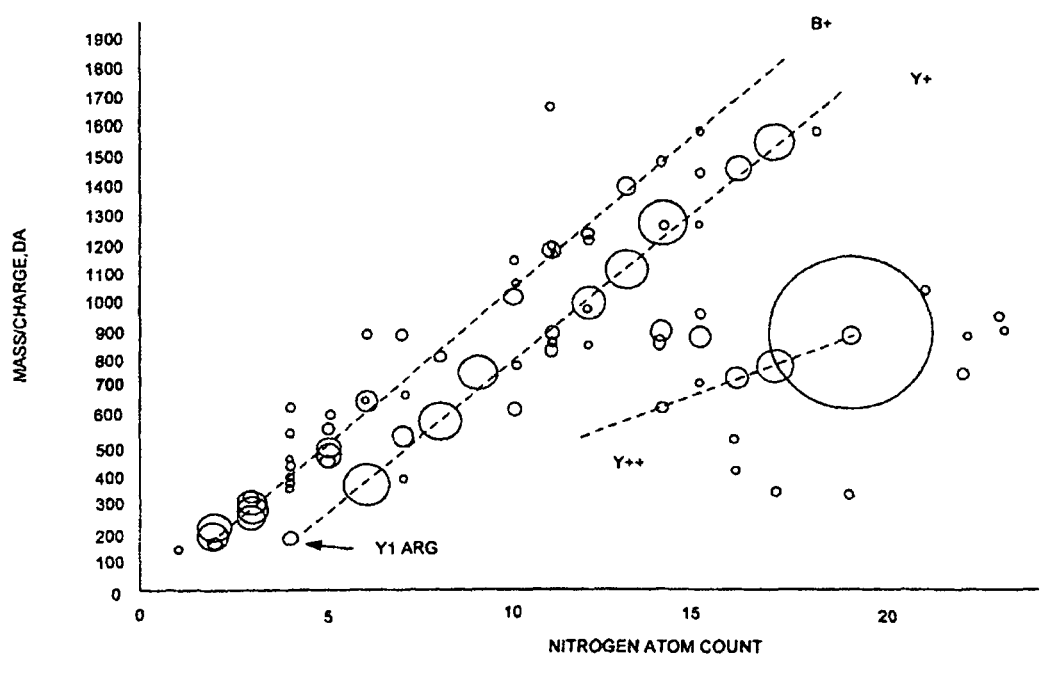
FIG. 8 is an exemplary plot of mass versus nitrogen atom count for the 15N/14N pairs of the spectrum shown in FIG. 7, in accordance with various embodiments.

FIG. 8 is an exemplary plot 800 of mass versus nitrogen atom count for the 15N/14N pairs of the spectrum shown in FIG. 7, in accordance with various embodiments. Plot 800 shows the low mass of every ion pair above a given threshold as a function of the nitrogen atom count. The size of the circle represents the intensity of the ion. Also shown are a number of straight lines that correspond to sequence ion series, both singly and double charged. The doubly charged sequence ions are prominent when viewed this way.

At several places in plot 800 there are ions at the same N atom count, particularly at low count values, and these are more related to the b ions than the y ions. Some of these ions may be artifacts, since the 15N-14N space is only one or two amu at these masses. It is also likely that others are due to internal fragments, scrambled b ions, or neutral losses. Plot 800 identifies them as sequence related and gives the opportunity for identification. Plot 800 also suggests a way to sequence peptides.

As an example, if the mass deltas between all ions containing 15 and 16 nitrogen atoms are examined, there are no matches corresponding to amino acids. Similarly, the differences between ions with 14 and 15 N atoms shows one likely residue (T), and the 13-14 difference suggests two residues, one of which is consistent with other masses (S).

Figure 9:
FIG. 9 is an exemplary table showing mass differences in the range 57 to 186 (the possible range for normal amino acids) between ions containing 14 and 16 N atoms, in accordance with various embodiments.

FIG. 9 is an exemplary table 900 showing mass differences in the range 57 to 186 (the possible range for normal amino acids) between ions containing 14 and 16 N atoms, in accordance with various embodiments. Thus table 1000 indicates the presence of a W (Trp) residue with 2 nitrogen atoms and a mass of 186.0739. Note also that the ions at m/z 634.2725 and 727.311, with 14 and 16 N atoms respectively, arise from doubly charged ions so the measured delta of 93.0382 in fact corresponds to 186.0764 and is additional evidence for the presence of W at this position.

Figure 10:
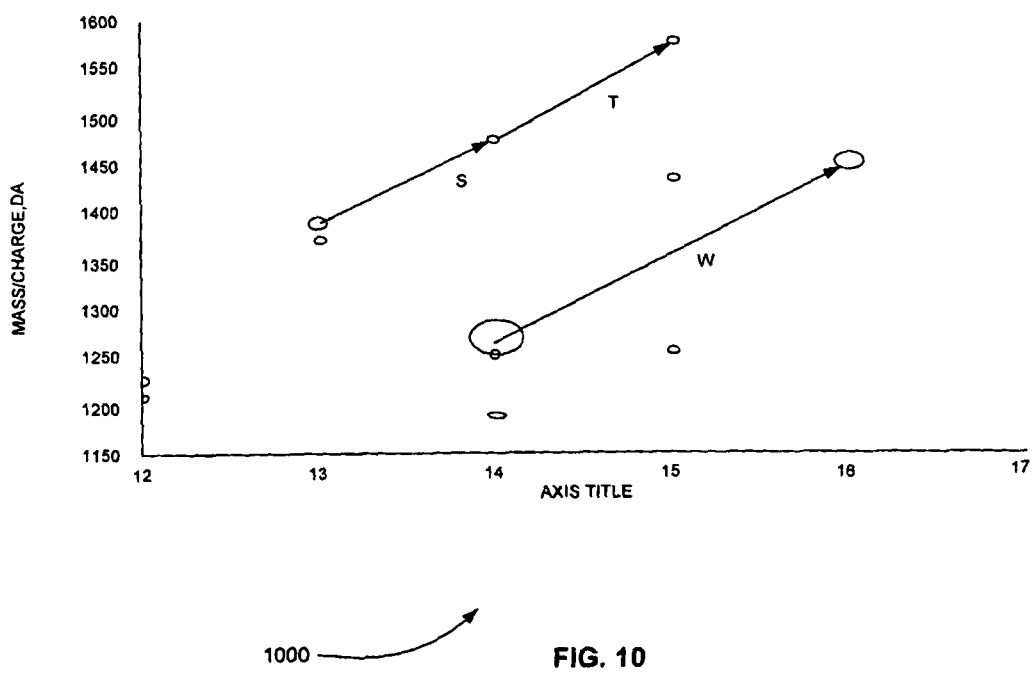
FIG. 10 is an exemplary plot of an expanded region of the mass versus nitrogen atom count plot shown in FIG. 8, in accordance with various embodiments.

FIG. 10 is an exemplary plot 1000 of an expanded region of the mass versus nitrogen atom count plot shown in FIG. 8, in accordance with various embodiments. Plot 1000 shows the assignment of amino acid residues for different mass ranges of nitrogen. Plot 1000 also shows that the ions can be assigned to the b and y series based on their orientation in the plot.

Figure 11:
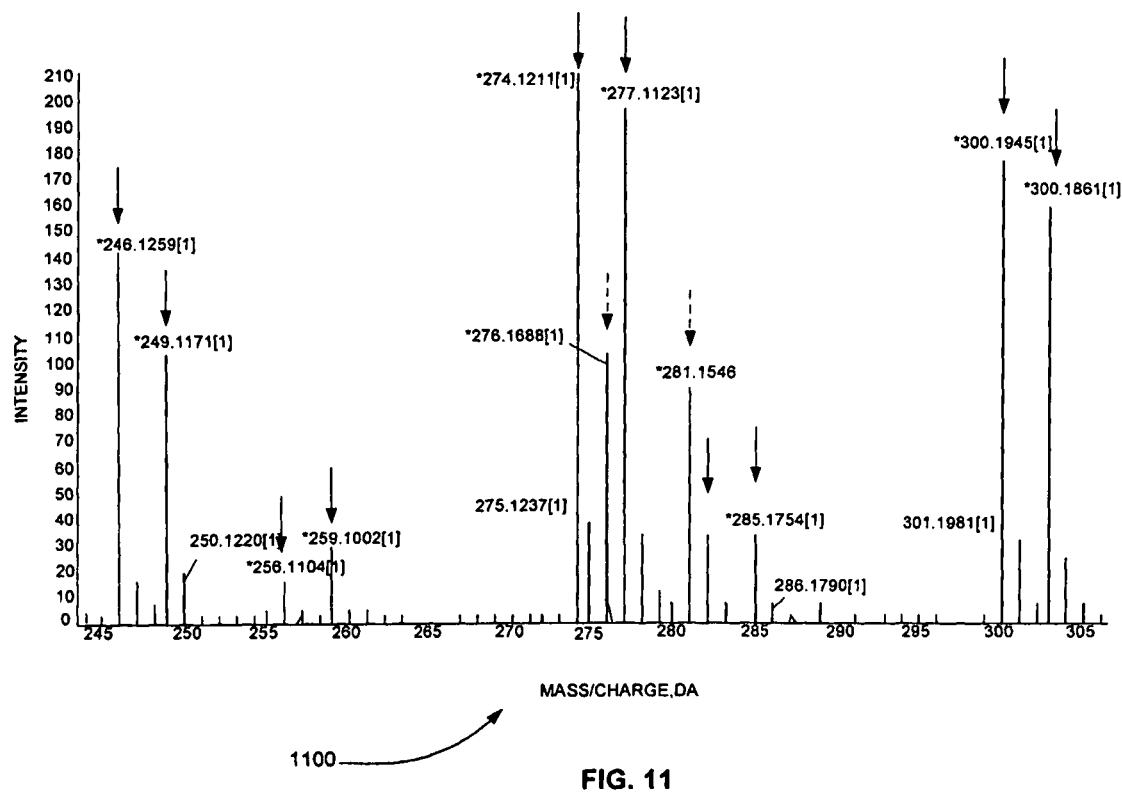
FIG. 11 is an exemplary plot of an expanded portion of the spectrum of peptide LVSWYDNEYGYSTR shown in FIG. 7, in accordance with various embodiments.

FIG. 11 is an exemplary plot 1200 of an expanded portion of the spectrum of peptide LVSWYDNEYGYSTR shown in FIG. 7, in accordance with various embodiments. In plot 1100, the majority of the peaks have 3 nitrogen atoms (solid arrows). However, the existence of a pair of peaks with 5 nitrogen atoms (dashed arrows) is also clear. Without recognizing the 15N-14N spacing difference, these pairs are not easily found.

Systems and Methods of Data Processing
Mass Spectrometry System

Figure 12:
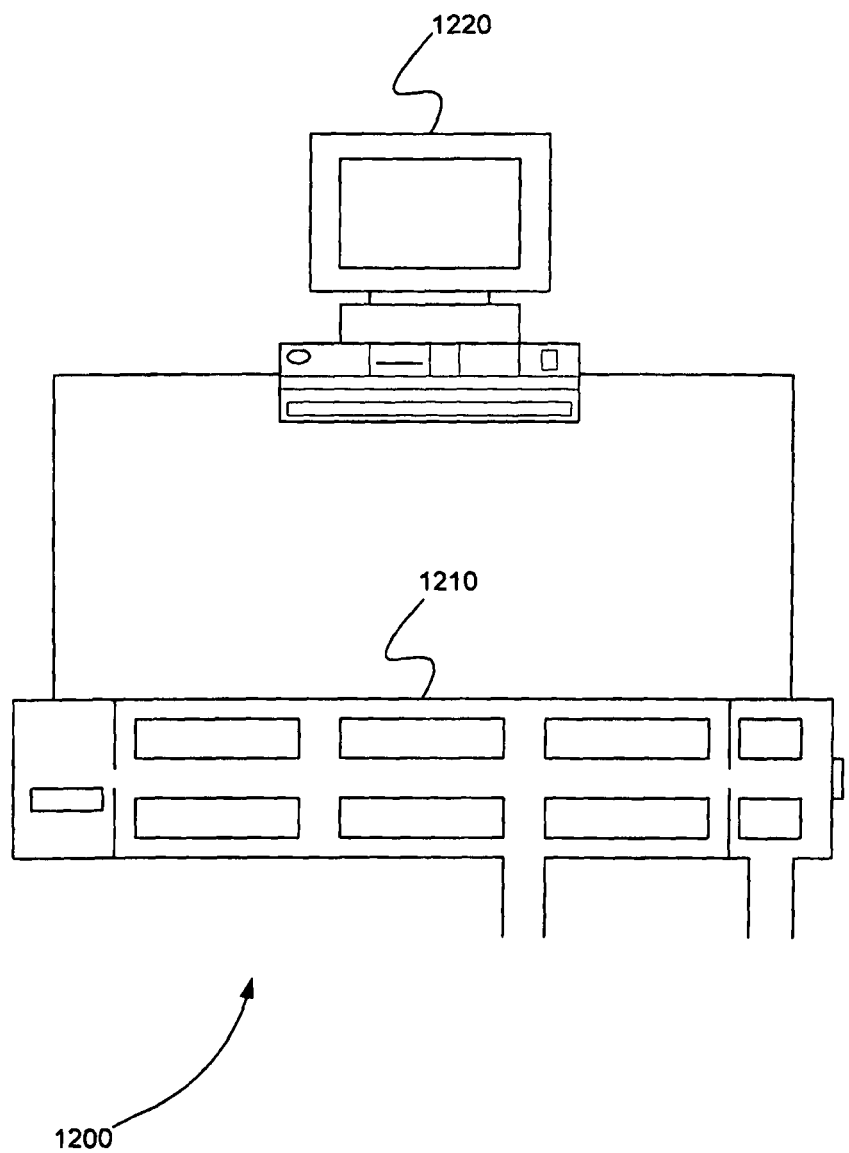
FIG. 12 is a schematic diagram showing a system for identifying the number of atoms of one or more elements present in an ion of a molecule using a mixture of different forms of the molecule, in accordance with various embodiments.

FIG. 12 is a schematic diagram showing a system 1200 for identifying the number of atoms of one or more elements present in an ion of a molecule using a mixture of different forms of the molecule, in accordance with various embodiments. System 1200 includes mass spectrometer 1210, and processor 1220. Processor 1220 can be, but is not limited to, a computer, microprocessor, or any device capable of sending and receiving control signals and data to and from mass spectrometer 1210 and processing data.

Mass spectrometer 1210 can be a tandem mass spectrometer, for example. Mass spectrometer 1210 can include can include one or more physical mass analyzers that perform two or more mass analyses. A mass analyzer of a mass spectrometer can include, but is not limited to, a time-of-flight (TOF), quadrupole, an ion trap, a linear ion trap, an orbitrap, or a Fourier transform mass analyzer. Mass spectrometer 1210 can include separate mass spectrometry stages or steps in space or time, respectively.

Mass spectrometer 1210 analyzes a mixture of at least two forms of a molecule using one or more ion scans across a mass range. Mass spectrometer 1210 produces a mass spectrum from the one or more ion scans for the mass range. The first form of the molecule includes a first combination of isotopes of one or more elements. The second form of the molecule includes a second combination of isotopes of the one or more elements. In various embodiments, isotope labeling is used to create the first form of the molecule and the second form of the molecule in the mixture.

Processor 1220 can be in communication with the mass spectrometer 1210. Processor 230 can be, but is not limited to, a computer, microprocessor, or any device capable of sending and receiving control signals and data to and from tandem mass spectrometer 220 and processing data.

Processor 1220 receives the mass spectrum produced by mass spectrometer 1210. Processor 1220 can receive the mass spectrum directly from mass spectrometer 1210, for example. In various embodiments, processor 1220 can receive the mass spectrum indirectly by reading the mass spectrum from a file stored on a memory, for example.

Processor 1220 locates a first peak and a second peak in the mass spectrum that differ in mass by a multiple of a mass difference between the first combination of isotopes and the second combination of isotopes. Processor 1220 identifies the number of atoms of the one or more elements present in an ion of the molecule from a mass difference between the first peak and the second peak.

In various embodiments, processor 1220 further locates a first peak and a second peak in the mass spectrum that differ in mass by a multiple of a mass difference between the first isotope and the second isotope and that have an intensity ratio substantially equal to the ratio of the amounts of the first form of the molecule and the second form of the molecule in the mixture.

In various embodiments, the at least two forms of the mixture analyzed by mass spectrometer 1210 include different isotopes of a single element. The first combination of isotopes includes a first isotope of the element. The second combination of isotopes includes a second isotope of the element. Processor 1220 locates a first peak and a second peak in the mass spectrum that differ in mass by a multiple of a mass difference between the first isotope and the second isotope. Processor 1220 identifies the number of atoms of the element from the multiple.

In various embodiments, the one or more elements include nitrogen (N). The first combination of isotopes includes 14N and the second combination of isotopes includes 15N, for example.

In various embodiments, the one or more elements include carbon (C). The first combination of isotopes includes 12C and the second combination of isotopes includes 13C, for example.

In various embodiments, the one or elements include hydrogen (H). The first combination of isotopes includes 1H and the second combination of isotopes includes 2H, for example.

In various embodiments, the one or elements include oxygen (O). The first combination of isotopes includes 16O and the second combination of isotopes includes 18O, for example.

In various embodiments, the one or elements include sulfur (S). The first combination of isotopes includes 32S and the second combination of isotopes includes 34S, for example.

In various embodiments, mass spectrometer 1210 is a tandem mass spectrometer and an ion of the molecule includes a product ion of a precursor ion obtained by MS/MS. The precursor ion includes a peptide and the product ion includes a peptide sequence ion, for example.

In various embodiments, processor 1220 uses a peptide sequence ion to determine a sequence of a peptide. If the first peak and the second peak described above are part of a first peak pair, processor 1220 can determine a sequence of a peptide. Processor 1220 locates a second peak pair that differ in mass by a multiple of a mass difference between the first combination of isotopes and the second combination of isotopes. Processor 1220 identifies a second number of atoms of the one or more elements present in a second ion of the molecule from a mass difference between peaks of the second peak pair. Finally, processor 1220 determines an amino acid residue of the sequence under two conditions. The first condition is that a mass difference between a first mass of the first peak pair and a second mass of the second peak pair is substantially equal to a mass of the amino acid. The second condition is that a difference between the number of atoms of the one or more elements and the second number of atoms of the one or more elements is equal to a number of atoms of the one or more elements in the amino acid residue. The first mass of the first peak pair is a low mass of the first peak pair and the second mass of the second peak pair is a low mass of the second peak pair, for example. Alternatively, the first mass of the first peak pair is a high mass of the first peak pair and the second mass of the second peak pair is a high mass of the second peak pair.

In various embodiments, processor 1220 further locates a terminus of the sequence. The terminus is an amino acid residue, for example. Processor 1220 locates the terminus of the sequence by locating a peak pair of the sequence that includes a mass that is substantially equal to one amino acid residue or that includes a mass that is substantially equal to a mass of the peptide, for example.

In various embodiments, processor 1220 further determines an orientation of the sequence from the terminus. Processor 1220 can determine that the orientation is C-terminal, for example. Processor 1220 calculates a terminus mass of the terminus amino acid residue and a terminus number of atoms of the one or more elements present in the terminus amino acid residue. Processor 1220 determines that the orientation is C-terminal, if the peptide is from a tryptic digestion and the terminus mass and the terminus number of atoms correspond to Arg or Lys.

Processor 1220 can also determine that the orientation is N-terminal, for example. Processor 1220 calculates a terminus mass of the terminus amino acid residue. Processor 1220 determines that the orientation is N-terminal, if another peak is found at another mass that is substantially equal the terminus mass minus a mass of CO (27.99419 amu). In other words, if another peak is found 27.99419 amu from either the high mass or the low mass of the peak pair that identifies the terminus mass, then the sequence orientation is N-terminal.

Mass Spectrometry Method

Figure 13:
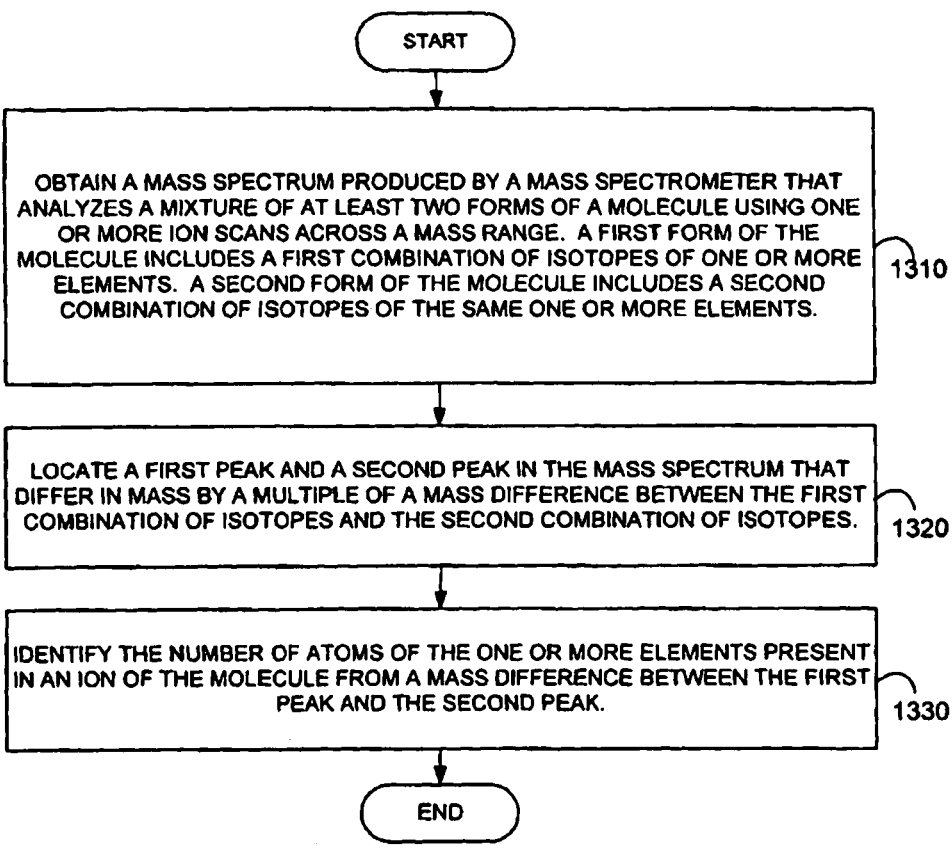
FIG. 13 is an exemplary flowchart showing a method for identifying the number of atoms of one or more elements present in an ion of a molecule using a mixture of different forms of the molecule, in accordance with various embodiments.

FIG. 13 is an exemplary flowchart showing a method 1300 for identifying the number of atoms of one or more elements present in an ion of a molecule using a mixture of different forms of the molecule, in accordance with various embodiments.

In step 1310 of method 1300, a mass spectrum produced by a mass spectrometer that analyzes a mixture of at least two forms of a molecule using one or more ion scans across a mass range is obtained. A first form of the molecule includes a first combination of isotopes of one or more elements. A second form of the molecule includes a second combination of isotopes of the same one or more elements.

In step 1320, a first peak and a second peak that differ in mass by a multiple of a mass difference between the first combination of isotopes and the second combination of isotopes are located in the mass spectrum.

In step 1330, the number of atoms of the one or more elements present in an ion of the molecule is identified from a mass difference between the first peak and the second peak.

Mass Spectrometry Computer Program Product

In various embodiments, a computer program product includes a non-transitory and tangible computer-readable storage medium whose contents include a program with instructions being executed on a processor so as to perform a method for identifying the number of atoms of one or more elements present in an ion of a molecule using a mixture of different forms of the molecule. This method is performed by a system that includes one or more distinct software modules.

Figure 14:
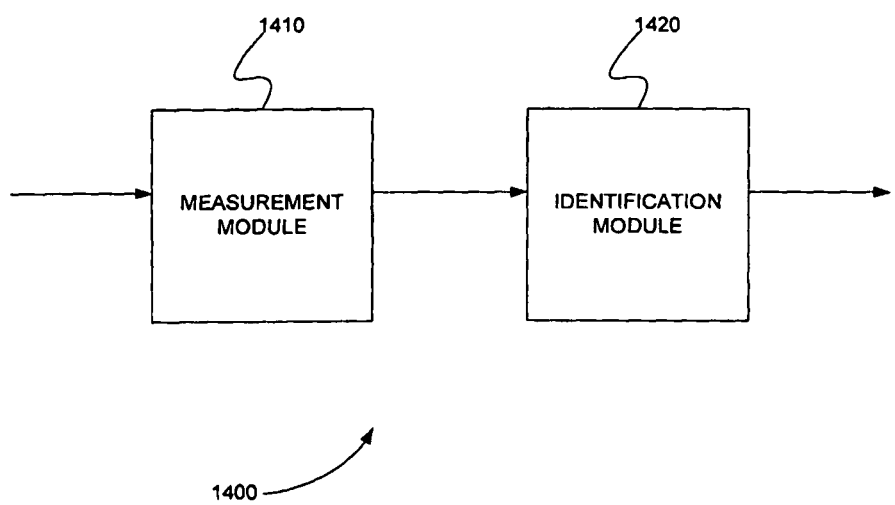
FIG. 14 is a schematic diagram of a system that includes one or more distinct software modules that performs a method for identifying the number of atoms of one or more elements present in an ion of a molecule using a mixture of different forms of the molecule, in accordance with various embodiments.

FIG. 14 is a schematic diagram of a system 1400 that includes one or more distinct software modules that performs a method for identifying the number of atoms of one or more elements present in an ion of a molecule using a mixture of different forms of the molecule, in accordance with various embodiments. System 1400 includes measurement module 1410 and identification 1420.

Measurement module 1410 obtains a mass spectrum produced by a mass spectrometer that analyzes a mixture of at least two forms of a molecule using one or more ion scans across a mass range. A first form of the molecule includes a first combination of isotopes of one or more elements. A second form of the molecule includes a second combination of isotopes of the same one or more elements.

Identification module 1420 locates a first peak and a second peak in the mass spectrum that differ in mass by a multiple of a mass difference between the first combination of isotopes and the second combination of isotopes. Identification module 1420 identifies the number of atoms of the one or more elements present in an ion of the molecule from a mass difference between the first peak and the second peak.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for identifying the number of atoms present in an ion of a molecule using a mixture of different forms of the molecule, comprising:
a mass spectrometer that analyzes a mixture of at least two forms of a molecule using one or more ion scans across a mass range and produces a mass spectrum from the one or more ion scans for the mass range, wherein a first form of the molecule includes a first combination of isotopes of one or more elements, and wherein a second form of the molecule includes a second combination of isotopes of the one or more elements; and
a processor in communication with the mass spectrometer that
locates a first peak and a second peak in the mass spectrum that differ in mass by a multiple of a mass difference between the first combination of isotopes and the second combination of isotopes, and
identifies a number of atoms of the one or more elements present in an ion of the molecule from a mass difference between the first peak and the second peak.

2. The system of claim 1, wherein the processor further locates a first peak and a second peak in the mass spectrum that differ in mass by a multiple of a mass difference between the first isotope and the second isotope and that have an intensity ratio substantially equal to the ratio of the amounts of the first form of the molecule and the second form of the molecule in the mixture.

3. The system of claim 1, wherein said one or more elements comprises an element, said first combination of isotopes comprises a first isotope of the element, said second combination of isotopes comprises a second isotope of the element, and the processor locates a first peak and a second peak in the mass spectrum that differ in mass by a multiple of a mass difference between the first isotope and the second isotope and identifies a number of atoms of the element from the multiple.

4. The system of claim 1, wherein the one or more elements are selected from the group consisting of nitrogen (N), carbon (C), hydrogen (H), oxygen (O), and sulfur (S).

5. The system of claim 4, wherein when one or more elements comprise nitrogen (N), the first combination of isotopes comprises 14N and the second combination of isotopes comprises 15N; wherein when one or more elements comprise carbon (C), the first combination of isotopes comprises 12C and the second combination of isotopes comprises 13C; wherein when one or more elements comprise hydrogen (H), the first combination of isotopes comprises 1H and the second combination of isotopes comprises 2H; wherein when one or more elements comprise oxygen (O), the first combination of isotopes comprises 16O and the second combination of isotopes comprises 18O; and wherein when one or more elements comprise sulfur (S), the first combination of isotopes comprises 32S and the second combination of isotopes comprises 34S.

6. The system of claim 1, wherein isotope labeling is used to create the first form of the molecule and the second form of the molecule in the mixture.

7. The system of claim 1, wherein the mass spectrometer comprises a tandem mass spectrometer and the ion of the molecule comprises a product ion of a precursor ion obtained by tandem mass spectrometry/mass spectrometry (MS/MS).

8. The system of claim 7, wherein the precursor ion comprises a peptide and the product ion comprises a peptide sequence ion.

9. The system of claim 8, wherein the processor uses the peptide sequence ion to determine a sequence of the peptide.

10. The system of claim 9, wherein the first peak and the second peak comprise a first peak pair and the processor determines a sequence of the peptide by
locating a second peak pair that differ in mass by a multiple of a mass difference between the first combination of isotopes and the second combination of isotopes,
identifying a second number of atoms of the one or more elements present in a second ion of the molecule from a mass difference between peaks of the second peak pair, and determining an amino acid residue of the sequence if a mass difference between a first mass of the first peak pair and a second mass of the second peak pair is substantially equal to a mass of the amino acid and if a difference between the number of atoms of the one or more elements and the second number of atoms of the one or more elements is equal to a number of atoms of the one or more elements in the amino acid residue.

11. The system of claim 10, wherein the first mass of the first peak pair is a low mass of the first peak pair and the second mass of the second peak pair is a low mass of the second peak pair, or wherein the first mass of the first peak pair is a high mass of the first peak pair and the second mass of the second peak pair is a high mass of the second peak pair.

12. The system of claim 10, wherein the processor further locates a terminus of the sequence.

13. The system of claim 12, wherein the processor locates a terminus of the sequence by locating a peak pair of the sequence that includes a mass that is substantially equal to one amino acid residue or that includes a mass that is substantially equal to a mass of the peptide.

14. The system of claim 12, wherein the processor further determines an orientation of the sequence from the terminus.

15. The system of claim 14, wherein the processor determines an orientation of the sequence from the terminus by
calculating a terminus mass of the terminus amino acid residue and a terminus number of atoms of the one or more elements present in the terminus amino acid residue and
determining that the orientation is C-terminal if the peptide is from a tryptic digestion and the terminus mass and the terminus number of atoms correspond to Arg or Lys.

16. The system of claim 14, wherein the processor determines an orientation of the sequence from the terminus by
calculating a terminus mass of the terminus amino acid residue and
determining that the orientation is N-terminal if another peak is found at another mass that is substantially equal the terminus mass minus a mass of CO (27.99419 amu).

17. A method for identifying the number of atoms present in an ion of a molecule using a mixture of different forms of the molecule, comprising:
obtaining a mass spectrum produced by a mass spectrometer that analyzes a mixture of at least two forms of a molecule using one or more ion scans across a mass range, wherein a first form of the molecule includes a first combination of isotopes of one or more elements, and wherein a second form of the molecule includes a second combination of isotopes of the one or more elements;
locating a first peak and a second peak in the mass spectrum that differ in mass by a multiple of a mass difference between the first combination of isotopes and the second combination of isotopes; and
identifying a number of atoms of the one or more elements present in an ion of the molecule from a mass difference between the first peak and the second peak.

18. A computer program product, comprising a non-transitory and tangible computer-readable storage medium whose contents include a program with instructions being executed on a processor so as to perform a method for identifying the number of atoms present in an ion of a molecule using a mixture of different forms of the molecule, the method comprising:
providing a system, wherein the system comprises one or more distinct software modules, and wherein the distinct software modules comprise a measurement module and an identification module;
obtaining a mass spectrum produced by a mass spectrometer that analyzes a mixture of at least two forms of a molecule using one or more ion scans across a mass range using the measurement module, wherein a first form of the molecule includes a first combination of isotopes of one or more elements, and wherein a second form of the molecule includes a second combination of isotopes of the one or more elements;
locating a first peak and a second peak in the mass spectrum that differ in mass by a multiple of a mass difference between the first combination of isotopes and the second combination of isotopes using the identification module; and
identifying a number of atoms of the one or more elements present in an ion of the molecule from a mass difference between the first peak and the second peak using the identification module.

* * * * *